United States Patent
Tai et al.

(10) Patent No.: US 10,131,716 B2
(45) Date of Patent: Nov. 20, 2018

(54) METHOD FOR MANUFACTURING FUNGAL PHARMACEUTICAL COMPOSITION

(71) Applicants: TAIWAN INDIGENA BOTANICA CO., LTD., Taipei (TW); TAIPEI MEDICAL UNIVERSITY, Taipei (TW)

(72) Inventors: Cheng-Jeng Tai, Taipei (TW); Yeu-Ching Shi, New Taipei (TW); Fang-Mo Chang, Taichung (TW); Ching-Hua Su, Taipei (TW)

(73) Assignees: Taiwan Indigena Botanica Co., Ltd. (TW); Taipei Medical University (TW)

( * ) Notice: Subject to any disclaimer, the term of this patent is extended or adjusted under 35 U.S.C. 154(b) by 0 days.

(21) Appl. No.: 15/384,382

(22) Filed: Dec. 20, 2016

(65) Prior Publication Data

US 2017/0342170 A1    Nov. 30, 2017

(30) Foreign Application Priority Data

May 25, 2016 (TW) .............................. 105116243 A

(51) Int. Cl.
| | |
|---|---|
| *A61K 36/74* | (2006.01) |
| *C08B 37/00* | (2006.01) |
| *A61K 31/726* | (2006.01) |
| *A61K 36/074* | (2006.01) |
| *A61L 27/20* | (2006.01) |
| *A61L 27/60* | (2006.01) |

(52) U.S. Cl.
CPC ........ *C08B 37/0063* (2013.01); *A61K 31/726* (2013.01); *A61K 36/074* (2013.01); *A61L 27/20* (2013.01); *A61L 27/60* (2013.01); *A61K 2236/33* (2013.01)

(58) Field of Classification Search
None
See application file for complete search history.

(56) References Cited

U.S. PATENT DOCUMENTS 7,524,504 B1 * 4/2009 Bishop ................... A61K 8/645
                                                                       424/195.15
9,623,074 B2 * 4/2017 Ou ........................ A61K 38/16

FOREIGN PATENT DOCUMENTS

TW         442 496        *  6/2001

OTHER PUBLICATIONS

Chuang, C. et al. Sacchachitin, A Novel Chitin-Polysaccharide Conjugate Macromolecule Present in Ganoderma lucidum. Pharaceutical Biology 51(1)84-95, Jan. 2013. (Year: 2013).*
Cheong J. et al. Characterization of an Alkali Extracted Peptidoglycan from Korean Ganoderma lucidum. Arch Pharm Res 22(5)515-519, 1999.*

* cited by examiner

*Primary Examiner* — Ralph J Gitomer

(57) ABSTRACT

The present invention provides a method for manufacturing fungal pharmaceutical composition, used for extracting a glycosaminoglycan fiber from a fungal cell wall. Differing from the glycosaminoglycan fiber produced by using a fabrication method proposed by Taiwan patent No. 442496 showing many drawbacks including low extraction percentage, coarse fiber, and having light-yellow color, the glycosaminoglycan fiber manufactured by using this novel method reveals the advantages of high extraction percentage, fine fibers, and showing white color. So that, the novel glycosaminoglycan fiber produced by using the present invention's method is suitable for being processed to an excipient. Moreover, because a variety of experimental results have proved that the glycosaminoglycan fiber produced by using the present invention's method possesses good adsorption ability of tissue fluid and moisture retention ability, this novel glycosaminoglycan fiber is also suitable for being processed to a skin dressing, an artificial skin, or a hydrate mask.

6 Claims, 10 Drawing Sheets

METHOD FOR MANUFACTURING FUNGAL PHARMACEUTICAL COMPOSITION

BACKGROUND OF THE INVENTION

1. Field of the Invention

The present invention relates to the technology field of medically-used compositions, and more particularly to a method for extracting a complex consisting of chitin and polysaccharides, so as to further process the complex to a fungal pharmaceutical composition.

2. Description of the Prior Art

Skin does not only possess the functionalities to modulate body temperature and maintain body water balance, but also be the first defensive line of human body for resisting the invasion of external pathogens. So that, when a man is subjected to a large area of skin damage, the man may eventually die due to the failure of body temperature modulation. In general, even if a skin wound has been treated with therapies, the skin wound still needs to contact with clothes, such that the condition of the skin wound may become more badly since the wound infected with dusts and germs through the clothes. Therefore, medical personnel usually cover a wound dressing on the treated wound for preventing from the invasion of external dusts or germs.

Gauzes or cotton pads are the traditional wound (skin) dressings commonly adopted by medical institutions. In practical application, such traditional wound dressings reveal following drawbacks:
(1) Although the gauzes or cotton pads can absorb a large amount of wound exudate (tissue fluid), the exudate often back infiltrate to the treated wound and skin near to the wound after the gauzes or cotton pads become hard; eventually, the nearby skin is corroded by the infiltrating exudate.
(2) It is well known that the healing of skin wound does rely on epithelial cells. So that, despite covering gauzes on the skin wound can prevent from the invasion of external dusts or germs, the hard and dry gauzes cause the epithelial cells be unable to nimbly drift in the skin wound, such that the skin wound's healing speed is therefore reduced.

For solving the drawbacks of the traditional skin dressings, Taiwan patent NO. 442496 has proposed a skin (wound) dressing made of poly(glucosamine) cellulose. The poly(glucosamine) cellulose, also called glycosaminoglycan fiber, is constructed by N-acetylglucosamine and (1→3)-β-D-glucan and can be manufactured by using following processing steps:

step (1'): preparing a specific fungus with 1000 g, and then smashing the specific fungus;
step (2'): immersing the product obtained from the step (1') by ethanol for 48 hours;
step (3'): collecting residues produced by the step (2'), and then drying the collected residues under 40° C.;
step (4'): treating the dried residues obtained from the step (3') by using 1N NaOH under 85° C., for 24 hours;
step (5'): using hypochlorite (0.1%) to decolor the product obtained from the step (4');
step (6'): using deionized water to repeatedly wash the product obtained from the step (5'), so as to obtain the product of poly(glucosamine) cellulose;
step (7'): collecting the poly(glucosamine) cellulose, and then producing a suspending liquid by adding the poly(glucosamine) cellulose in to deionized water;
step (8'): treating the suspending liquid with a pressure filtration process by using a filter paper, and then a specific thin film called SACCHACHITIN is formed on the filter paper.

Although the said SACCHACHITIN has proven by experimental data to be a skin (wound) dressing, the skin dressing made of the SACCHACHITIN still reveals following drawbacks:
(1) Because it can merely obtain the glycosaminoglycan fiber with 8-12 gram from 100-gram fungus, the extraction percentage of the glycosaminoglycan fiber fabricating method proposed by Taiwan patent NO. 442496 is too low (about 8-12%).
(2) Moreover, the glycosaminoglycan fiber fabricated by using the method of Taiwan patent NO. 442496 possesses coarse fibers and shows appearance color of light yellow.
(3) The most important is that, the glycosaminoglycan fiber fabricated by using the method of Taiwan patent NO. 442496 does not show good ability on wound exudate absorption and wound moisturization.

Thus, because the traditional skin dressings and the conventional skin dressing proposed by Taiwan patent NO. 442496 reveal practically-used drawbacks and shortcomings, the inventor of the present application has made great efforts to make inventive research thereon and eventually provided a method for manufacturing fungal pharmaceutical composition.

SUMMARY OF THE INVENTION

The primary objective of the present invention is to provide a method for manufacturing fungal pharmaceutical composition, wherein the method is used for extracting a glycosaminoglycan fiber from a fungal cell wall. Differing from the glycosaminoglycan fiber produced by using a fabrication method proposed by Taiwan patent No. 442496 showing the drawbacks of low extraction percentage, coarse fiber, and having light-yellow color, the glycosaminoglycan fiber manufactured by using this novel method reveals the advantages of high extraction percentage, fine fibers, and showing white color. So that, the novel glycosaminoglycan fiber produced by using the present invention's method is suitable for being processed to an excipient. Moreover, because a variety of experimental results have proved that the glycosaminoglycan fiber produced by using the present invention's method possesses good adsorption ability of tissue fluid and moisture retention ability, this novel glycosaminoglycan fiber is also suitable for being processed to a skin dressing, an artificial skin, or a hydrate mask.

In order to achieve the primary objective of the present invention, the inventor of the present invention provides an embodiment of the method for manufacturing fungal pharmaceutical composition, comprising following steps:

step (1): preparing a specific edible fungus with a specific weight, and then smashing the specific edible fungus by pounding for a smashing time, so as to obtain a smashed fungus;
step (2): turning over the smashed fungus, and then tanning the smashed fungus for a tanning time;
step (3): spreading the smashed fungus, and then grinding the smashed fungus for obtaining a grinded fungus;
step (4): immersing the grinded fungus in an organic solvent;

step (5): collecting a fungus residue from the organic solvent, and then drying the fungus residue under a first drying temperature;

step (6): applying a first alkali treatment to the fungus residue by using a first alkali solution;

step (7): applying a second alkali treatment to the fungus residue by using a second alkali solution;

step (8): collecting the fungus residue by using a first filtering sieve, and then using water to wash the fungus residue;

step (9): using deionized water to wash the fungus residue, and then collecting the fungus residue by using a second filtering sieve;

step (10): applying a decoloring treatment to the fungus residue by using a bleaching agent; and step (11) using deionized water to wash the fungus residue, and then a fungal pharmaceutical composition is obtained.

In the aforesaid embodiment of the method for manufacturing fungal pharmaceutical composition, the specific weight is in a range from 200 g to 500 g.

In the aforesaid embodiment of the method for manufacturing fungal pharmaceutical composition, the smashing time is in a range from 5 minutes to 15 minutes and the tanning time is in a range from 5 minutes to 30 minutes.

In the aforesaid embodiment of the method for manufacturing fungal pharmaceutical composition, the organic solvent is selected from the group consisting of: methanol, ethanol and propanol.

In the aforesaid embodiment of the method for manufacturing fungal pharmaceutical composition, the first alkali solution is mixed by 10-12N NaOH and 10-12N KOH according to a mixing ratio, and the mixing ratio is in a range from 1:11 to 1:5.

In the aforesaid embodiment of the method for manufacturing fungal pharmaceutical composition, the second alkali solution is mixed by 1-5N NaOH and 1-5N KOH according to a mixing ratio, and the mixing ratio is in a range from 1:11 to 1:5.

In the aforesaid embodiment of the method for manufacturing fungal pharmaceutical composition, both the first filtering sieve and the second filtering sieve have 20-80 mesh.

In the aforesaid embodiment of the method for manufacturing fungal pharmaceutical composition, the bleaching agent is selected from the group consisting of: ozone, hydrogen peroxide, and combination of the ozone and the hydrogen peroxide.

In the aforesaid embodiment of the method for manufacturing fungal pharmaceutical composition, the fungal pharmaceutical composition obtained from the step (11) is a glycosaminoglycan fiber, and the glycosaminoglycan fiber is constructed by N-acetylglucosamine and $(1\rightarrow3)$-$\beta$-D-glucan.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a method for manufacturing fungal pharmaceutical composition according to the present invention, embodiments of the present invention will be described in detail with reference to the attached drawings hereinafter.

Fungal cell wall, the outer covering of fungus, is formed through the intercross and interstack of polysaccharides and chitin. As the person skilled in fungus technology field well knows, the fungal cell wall can not only prevent from the invasion of destructive macromolecules (such as lytic enzymes), but also possesses a specific permeability. Moreover, the polysaccharides are found to be the primary constructing composition for forming the fungal cell wall. On the other hand, because chitin has the advantages of good biocompatibility, without toxicity, low price, easy to be modified, good mechanical strength, chitin is often processed to a bead, fiber, film, or gel according different bio-applications.

Figure 1A:
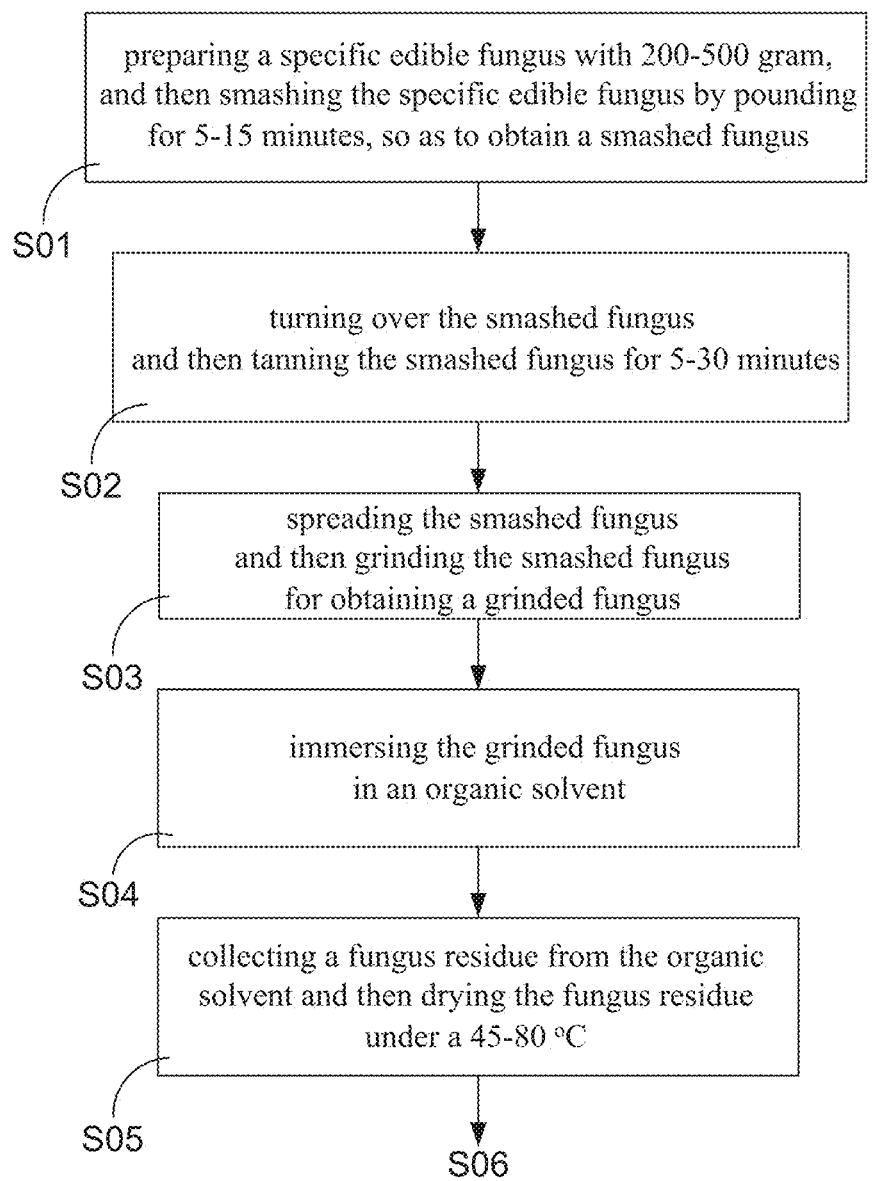
FIGS. 1A and 1B show flow chart diagrams of a method for manufacturing fungal pharmaceutical composition according to the present invention.
Figure 1B:
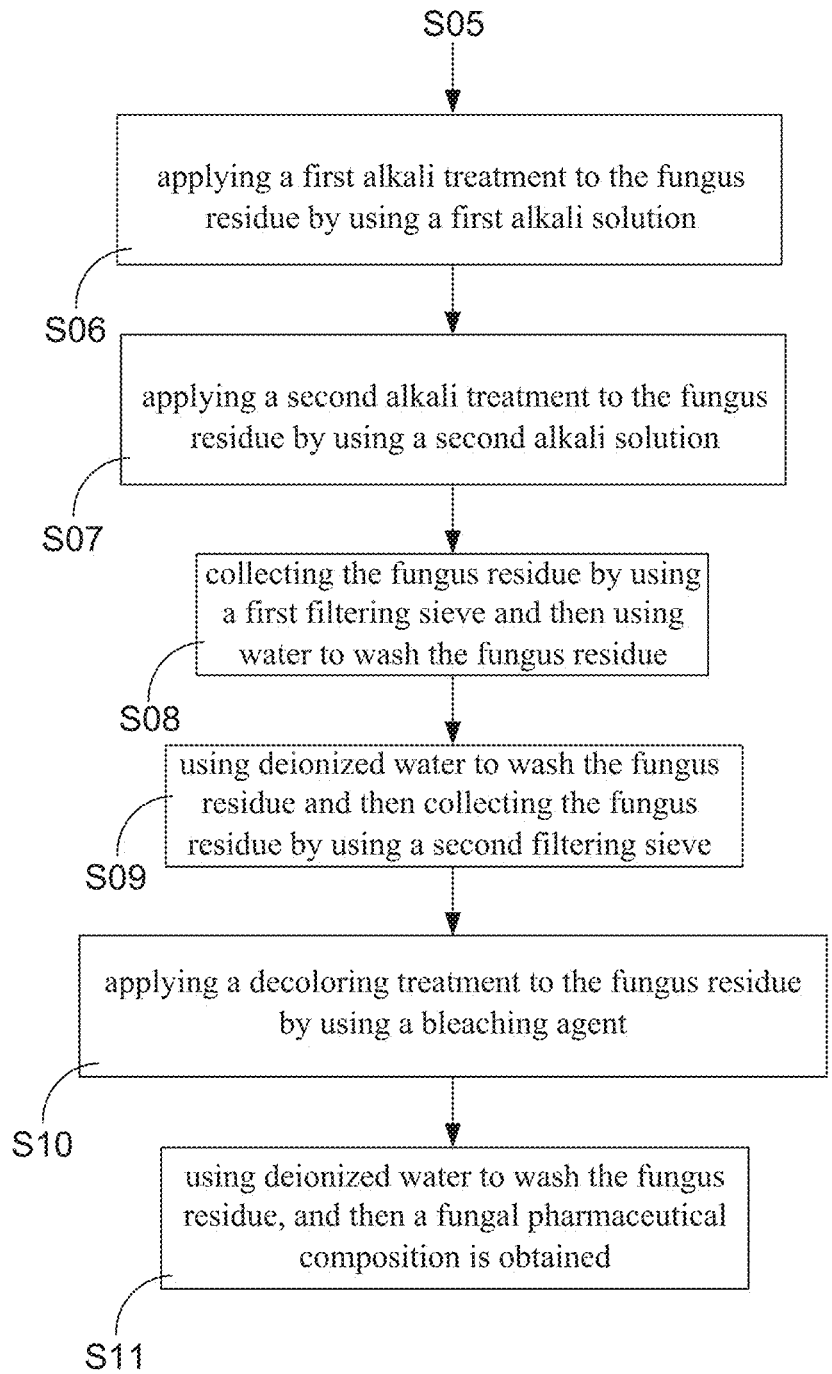

In the present invention, a particular method is proposed for extracting a complex consisting of chitin and polysaccharides from a fungal cell wall, wherein the complex is called SACCHACHITIN, and the SACCHACHITIN is a glycosaminoglycan fiber constructed by N-acetylglucosamine and $(1\rightarrow3)$-$\beta$-D-Glucan. Please refer to FIG. 1A and FIG. 1B, where provide flow chart diagrams of the method for manufacturing fungal pharmaceutical composition according to the present invention. As FIG. 1A and FIG. 1B show, this fungal pharmaceutical composition manufacturing method mainly comprises 11 steps.

First of all, the method proceeds to step (S01) for preparing a specific edible fungus with 200-500 gram and then smashing the specific edible fungus by pounding for 5-15 minutes, so as to obtain a smashed fungus. It needs to further explain that, the aforesaid edible fungus can be a fungal mycelium, a fungal sporocarp, or a post-extraction residue of the fungal mycelium, and the present invention takes a *ganoderma lucidum* as the exemplary edible fungus for finished all the manufacturing process steps.

After finishing the step (S01), the method is next proceeded to step (S02) for turning over the smashed fungus and then tanning the smashed fungus for 5-30 minutes. Continuously, the method proceeds to step (S03) for spreading the smashed fungus and then grinding the smashed fungus for obtaining a grinded fungus. Next, the method proceeds to step (S04) for immersing the grinded fungus in an organic solvent, wherein the organic solvent is a lower alcohol such as methanol, ethanol and propanol.

Subsequently, the method is proceeded to step (S05) for collecting a fungus residue from the organic solvent and then drying the fungus residue under a 45-80° C. It is worth explaining that, the organic solvent is used for extracting polysaccharide from the *ganoderma lucidum*. However, as the person skilled in fungus technology field well knows, no matter using hot water or ethanol to extract polysaccharide from the *ganoderma lucidum*, it is able to collect a large amount of *ganoderma lucidum* residue (~90% dry weight) after completing the extracting process. Therefore, in order to extract great amount of chitin and polysaccharide from the *ganoderma lucidum*, it must collect the fungus residue from the organic solvent through the step (S05).

After completing the step (S05), the method is next proceeded to step (S06) for applying a first alkali treatment to the fungus residue by using a first alkali solution. The arm of the first alkali treatment is to destruct protein and lipid in the *ganoderma lucidum*. In addition, the first alkali treatment can also break down the chemical bonds in the *ganoderma lucidum*, so as to increase the dissolution of polysaccharide extracted from the fungal cell wall. On the other hand, the deacetylation induced by the alkali treatment can modify chitin to chitosan. In the present invention, the first alkali treatment in the step (S06) is completed under a specific processing condition for 20-40 minutes, and the specific processing condition comprising a stirring speed of 120 rpm and a treating temperature of 80-100° C. Moreover, the first alkali solution is mixed by 10-12N NaOH and 10-12N KOH according to a mixing ratio, and the mixing ratio being in a range from 1:11 to 1:5.

Continuously, the method proceeds to step (S07) for applying a second alkali treatment to the fungus residue by using a second alkali solution. In the present invention, the second alkali treatment in the step (S07) is completed under a specific processing condition for 2-8 hours, and the specific processing condition comprising a stirring speed of 120 rpm and a treating temperature of 80-100° C. Moreover, the second alkali solution is mixed by 1-5N NaOH and 1-5N KOH according to a mixing ratio, and the mixing ratio being in a range from 1:11 to 1:5.

After completing the step (S07), the method is next proceeded to step (S08) for collecting the fungus residue by using a first filtering sieve and then using water to wash the fungus residue. The method subsequently proceeds to step (S09) for using deionized water to wash the fungus residue and then collecting the fungus residue by using a second filtering sieve. In the present invention, both the first filtering sieve and the second filtering sieve have 20-80 mesh. Next, the method is proceeded to step (S10) for applying a decoloring treatment to the fungus residue by using a bleaching agent. In the present invention, the decoloring treatment in the step (10) is completed under a specific processing condition for 80 minutes, and the specific processing condition comprising a stirring speed of 120 rpm and a treating temperature of 80-100° C. Moreover, the bleaching agent can be ozone, hydrogen peroxide, and combination of the ozone and the hydrogen peroxide. Preferably, the present invention takes hydrogen peroxide (25-45%) as the exemplary bleaching agent for finished the step (S10).

Eventually, in step (S11), deionized water is adopted for washing the fungus residue, and then a fungal pharmaceutical composition is obtained. The fungal pharmaceutical composition obtained from the step (S11) is a glycosaminoglycan fiber with a specific fiber length of 10-50 μm. The collected glycosaminoglycan fiber can be added into deionized water for forming a suspending liquid; and then, after treating the suspending liquid with a pressure filtration process by using a filter paper, a specific thin film called SACCHACHITIN is formed on the filter paper. Herein, it needs to further explain that, the SACCHACHITIN is constructed by N-acetylglucosamine and (1→3)-β-D-glucan, and can be further processed to an artificial skin, a wound dressing, or a mask.

The SACCHACHITIN can also be processed to an excipient through following processing steps:

step (S121): applying a hot air drying treatment to the SACCHACHITIN obtained from the step (S11) under 45-85° C., for 30-60 minutes; and step (S122): applying a hot air drying treatment to the SACCHACHITIN obtained from the step (S11); and step (S123): smashing the SACCHACHITIN, and then collecting the SACCHACHITIN having a specific fiber length of 50-200 μm by filtering.

Comparing to traditional wound dressings and the skin dressing proposed by Taiwan patent NO. 442496, the fungal pharmaceutical composition (i.e., the glycosaminoglycan fiber named SACCHACHITIN) reveals many advantages. Please refer to FIG. 2, which shows a statistics bar chart of different dressing samples versus extraction percentage. Introductions for the dressing samples of FIG. 2 are provided by following Table (1).

TABLE 1

| Dressing sample | Introduction |
|---|---|
| NO. 1 | Dressing sample NO. 1 is produced by using the fabrication method proposed by Taiwan patent NO. 442496 |
| NO. 2 | Dressing sample NO. 1 is produced by using a specific fabrication method established by modifying the fabrication method proposed by Taiwan patent NO. 442496, wherein the modifications include:<br>(1) increasing the percentage of smashed fungus in the step (1'); and<br>(2) reducing the alkali treatment time from 24 hours to 2-8 hours in the step (4'). |
| NO. 3 | Dressing sample NO. 3 is produced by using a specific fabrication method established by modifying the fabrication method proposed by Taiwan patent NO. 442496, wherein the modifications include:<br>(1) increasing the percentage of smashed fungus in the step (1');<br>(2) in the step (4'), a high-concentration alkali solution is firstly used for completing a first alkali treatment and then a low-concentration alkali solution is subsequently used for carrying out a second alkali treatment;<br>(3) reducing the alkali treatment time from 24 hours to 2-8 hours in the step (4'). |
| NO. 4 | Dressing sample NO. 4 is produced by using the present invention's manufacturing method. |

Figure 2:
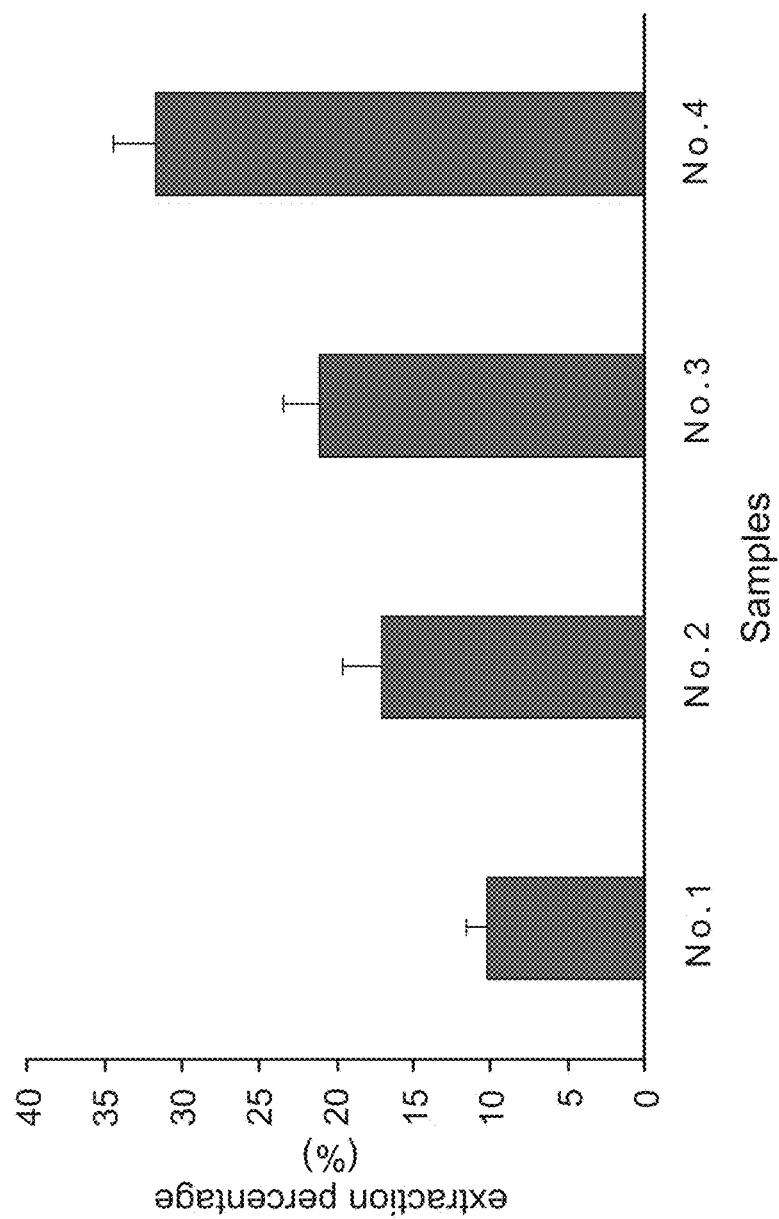
FIG. 2 shows a statistics bar chart of different dressing samples versus extraction percentage.

From FIG. 2, it is able to find that, the extraction percentage of glycosaminoglycan fiber produced by using the fabrication method proposed by Taiwan patent NO. 442496 is merely 8-12%. However, the extraction percentage of glycosaminoglycan fiber produced by using the present invention's manufacturing method is up to 25-35%. That is, there has glycosaminoglycan fiber with 25-35 gram can be obtained when taking 100-gram fungus as raw material.

Figure 3:
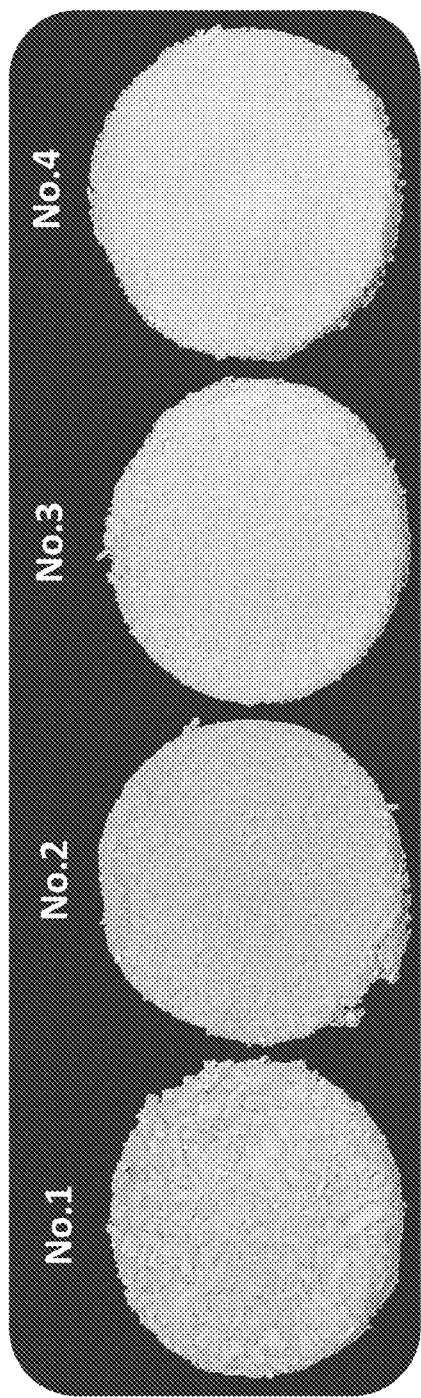
FIG. 3 shows image diagrams of the different dressing samples.

Please continuously refer to FIG. 3, where image diagrams of the different samples are provided. From FIG. 3, it can find that the glycosaminoglycan fiber (SACCHACHITIN) by using the fabrication method of Taiwan patent NO. 442496 possesses coarse fibers and shows appearance color of light yellow. However, the extraction percentage of glycosaminoglycan fiber produced by using the present invention's manufacturing method possesses fine fibers and shows appearance color of white color. So that, the novel glycosaminoglycan fiber produced by using the present invention's method is suitable for being processed to an excipient.

Tissue Fluid Absorption Test:

An absorption test is completed for proving the glycosaminoglycan fiber produced by using the present invention's method is suitable for being a (dry) skin dressing. Before starting the absorption test, various skin dressings, including non-stick dressing, gauze, gel dressing, Hydrophilic dressing, artificial skin, dressing sample NO. 1, dressing sample NO. 2, dressing sample NO. 3, and dressing sample NO. 4, are prepared and cut so as to have a specific size ranged from 1×1 cm$^2$ to 1.5×1.5 cm$^2$ and a specific weight ranged from 0.02 g to 0.05 g. When executing the absorption test, tissue fluid with 100-200 mL is dropped onto each of the skin (wound) dressings, and it can find that the Hydrophilic dressing and the artificial skin cannot rapidly absorb the tissue fluid. Moreover, both the Hydrophilic dressing and the artificial skin are measured to have a maximum tissue fluid capability of 80-120 mL.

Comparing to the Hydrophilic dressing and the artificial skin, the non-stick dressing, the gauze, the dressing sample NO. 1, the dressing sample NO. 2, the dressing sample NO. 3, and the dressing sample NO. 4 can rapidly absorb the tissue fluid. Moreover, the inventors of the present invention also find that the dressing sample NO. 1, the dressing sample NO. 2, the non-stick dressing, and the gauze are unable to absorb and carry the tissue fluid when the dropping volume of the tissue fluid is over 250-400 mL. After finishing the absorption test, the dressing sample NO. 3 and the dressing sample NO. 2 are measured to have a maximum tissue fluid capability of 600-800 mL. So that, the absorption test has proved that the glycosaminoglycan fiber produced by using present invention's method is also suitable for being processed to a (dry) skin dressing.

Figure 4:
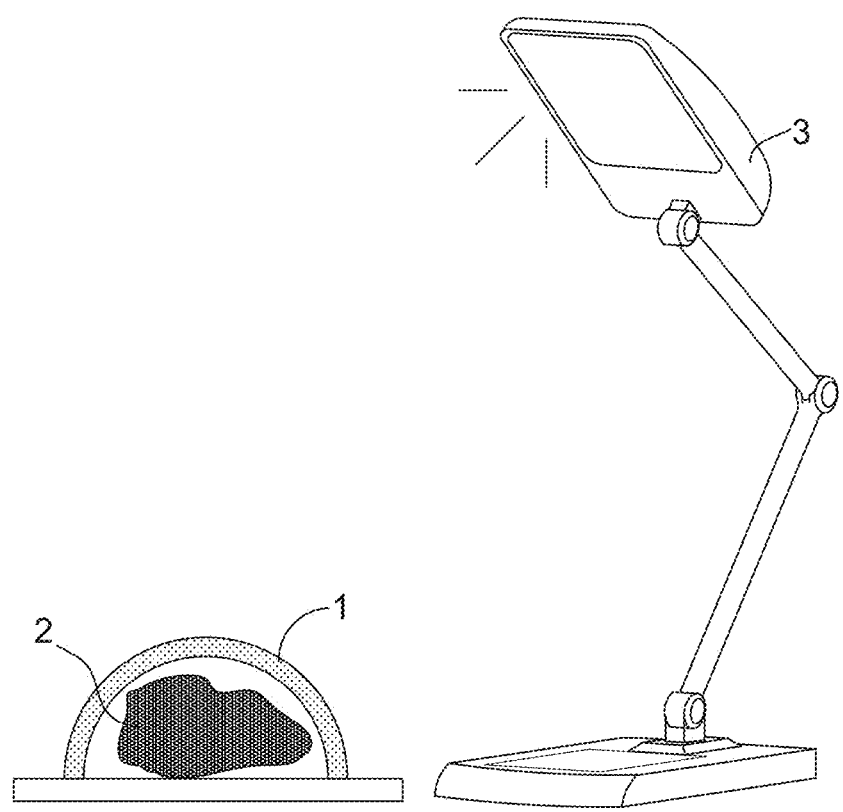
FIG. 4 shows a schematic framework view of a moisture retention capability test.
Figure 5A:
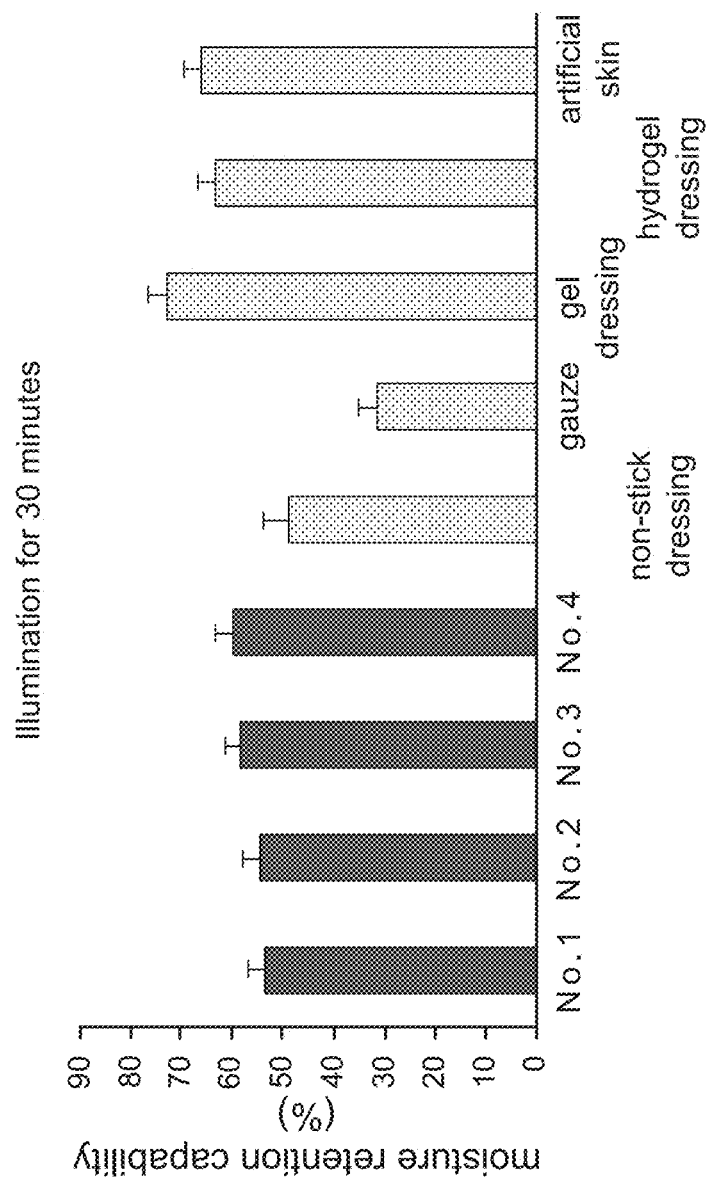
FIG. 5A and FIG. 5B show two statistics bar charts of different dressing samples versus moisture retention capability.
Figure 5B:
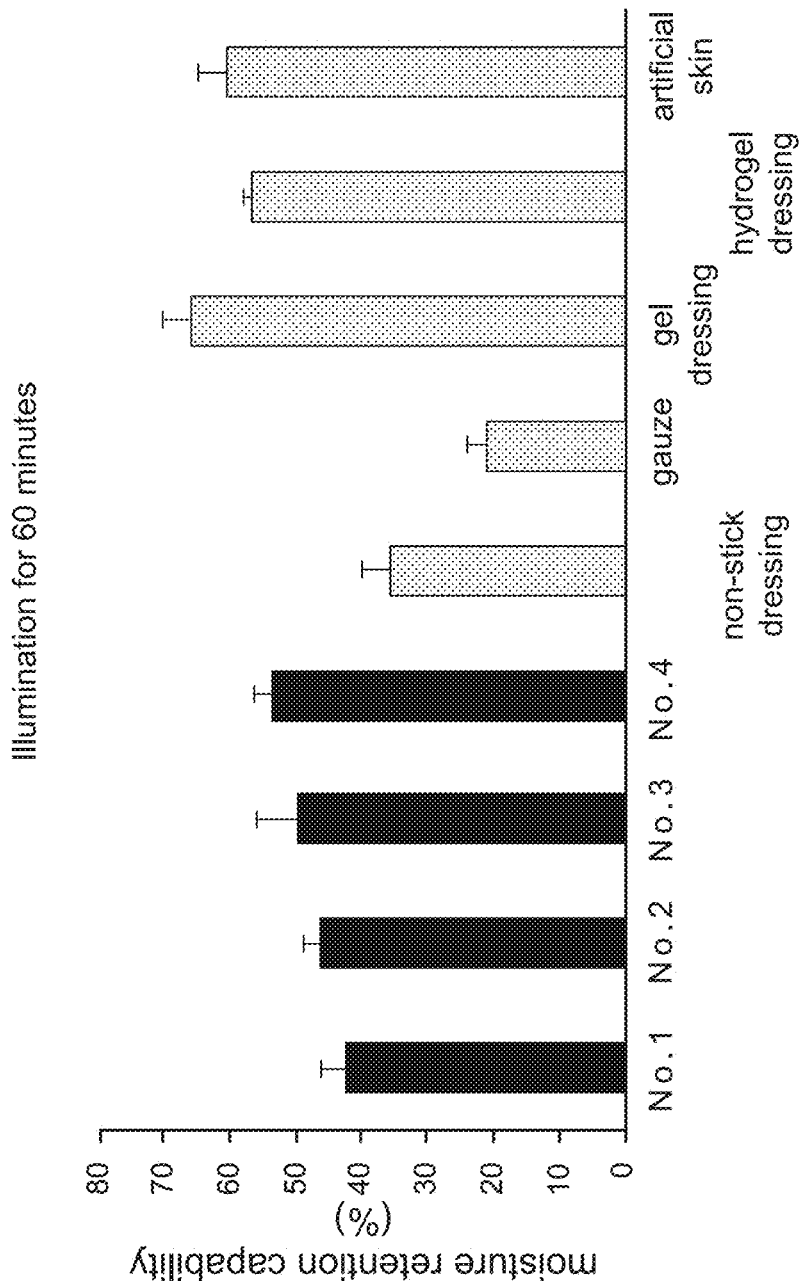

Moisture Retention Capability Test:

A moisture retention capability test is completed for proving the glycosaminoglycan fiber produced by using the present invention's method is suitable for being a (wet) skin dressing, an artificial skin, or a hydrate mask. Please refer to FIG. 4, which illustrates a schematic framework diagram of the moisture retention capability test. As FIG. 4 shows, the testing dressing 1 is covered on tissue fluid 2 and illuminated by a halogen lamp 3. Please refer to FIG. 5A and FIG. 5B, where two statistics bar charts of different samples versus moisture retention capability are provided. From FIG. 5A, it is able to know that the ranking of the moisture retention capability of the testing dressings is as follows: 1$^{st}$: gel dressing; 2$^{nd}$: artificial skin and hydrophilic dressing; 3$^{rd}$: dressing sample NO. 3 and dressing sample NO. 4; 4$^{th}$: dressing sample NO. 1, dressing sample NO. 2, and non-stick dressing; 5$^{th}$: gauze. Moreover, From FIG. 5B, it is able to know that the ranking of the moisture retention capability of the testing dressings is as follows: 1$^{st}$: gel dressing; 2$^{nd}$: artificial skin; 3$^{rd}$: hydrophilic dressing; 4$^{th}$: dressing sample NO. 4; 5$^{th}$: dressing sample NO. 2 and dressing sample NO. 3; 6$^{th}$: dressing sample NO. 1; 7$^{th}$: non-stick dressing; 8$^{th}$: gauze. So that, the moisture retention capability test has proved that the glycosaminoglycan fiber produced by using present invention's method is also suitable for being processed to a (wet) skin dressing, an artificial skin, or a hydrate mask.

Figure 6:
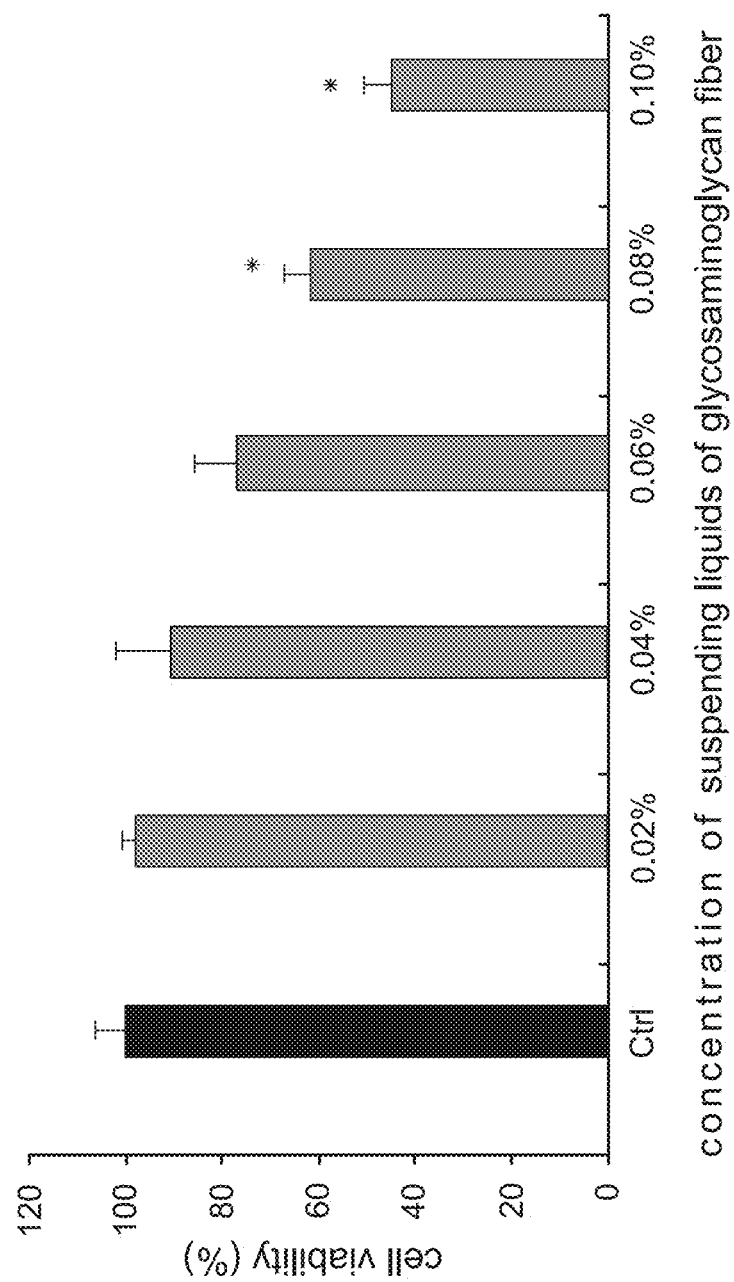
FIG. 6 shows a statistics bar chart of different suspending liquids versus cell viability.

Cytotoxicity Test:

A cytotoxicity test is completed for verifying the biosafety of the glycosaminoglycan fiber produced by using the present invention's method. Before starting the cytotoxicity test, the glycosaminoglycan fiber is processed to a glycosaminoglycan powder consisting of nanoparticles, and then the glycosaminoglycan powder is further fabricated to various suspending liquids with different glycosaminoglycan powder concentration. Continuously, the cytotoxicity test is carried out after treating human diploid cell WI-38 with the various suspending liquids. Please refer to FIG. 6, which shows a statistics bar chart of different suspending liquids versus cell viability. From FIG. 6, it is able to know that, the suspending liquids having the glycosaminoglycan powder concentration exceeding 0.08% would cause toxic reaction to cell WI-38.

Collagenase Activity Test Test:

A collagenase activity test is completed for determining whether the glycosaminoglycan fiber is able to stimulate the growth of collagen and then promote the healing speed of skin wounds. During the collagenase activity test, various suspending liquids with different glycosaminoglycan powder concentration (0.01-0.05%) are used to treat human diploid cell WI-38.

Figure 7:
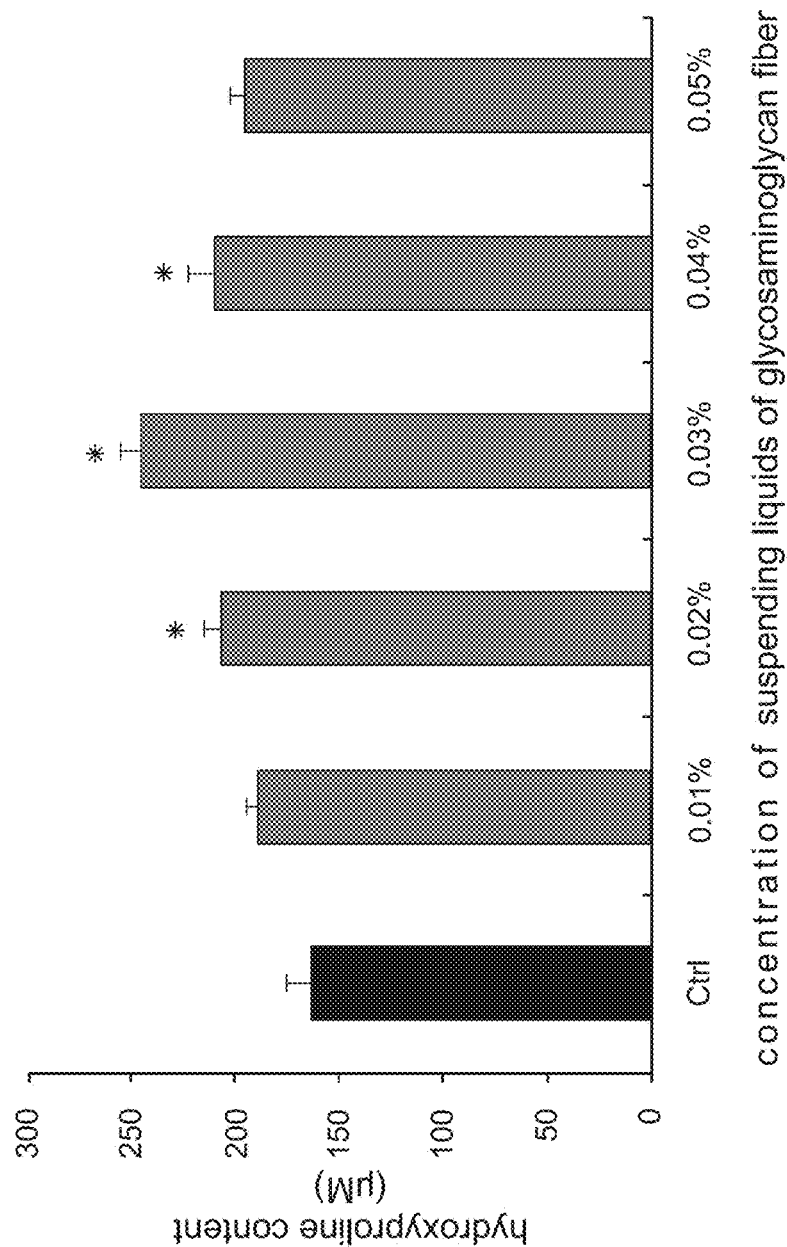
FIG. 7 shows a statistics bar chart of different suspending liquids versus hydroxyproline content.
Figure 8:
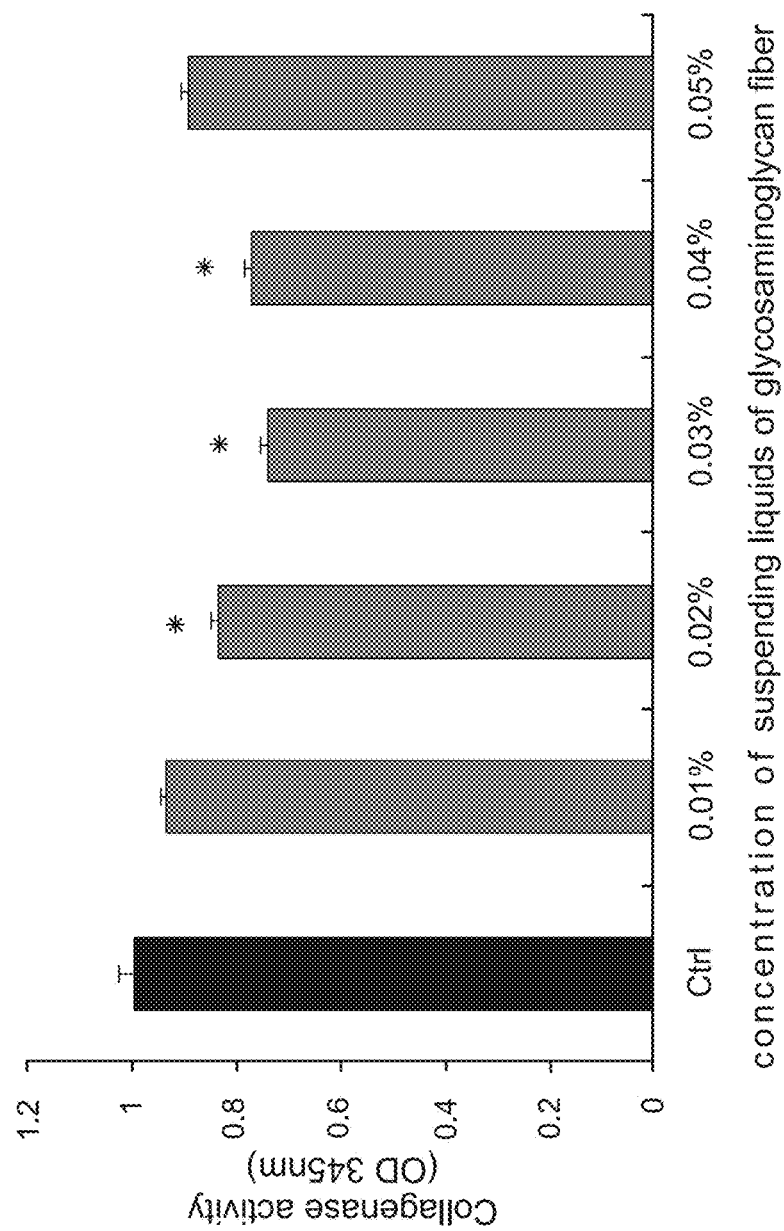
FIG. 8 shows a statistics bar chart of different suspending liquids versus collagenase activity.

Please refer to FIG. 7, which shows a statistics bar chart of different suspending liquids versus hydroxyproline content. From FIG. 7, it can easily find that, the suspending liquids with 0.02-0.04% glycosaminoglycan powder concentration can enhance the activity of hydroxyproline. The hydroxyproline is a primary ingredient for stimulating the cell WI-38 producing the collagen. Moreover, please continuously refer to FIG. 8, which shows a statistics bar chart of different suspending liquids versus collagenase activity. From FIG. 8, it can easily find that, the suspending liquids with 0.02-0.04% glycosaminoglycan powder concentration can inhibit the activity of collagenase. The inhibition of collagenase activity can reduce the decomposition level of the collagen in the cell WI-38.

Therefore, through above descriptions, the method for manufacturing fungal pharmaceutical composition provided by the present invention has been introduced completely and clearly; in summary, the present invention includes the advantages of:

(1) Differing from the glycosaminoglycan fiber produced by using a fabrication method proposed by Taiwan patent No. 442496 showing many drawbacks including low extraction percentage, coarse fiber, and having light-yellow color, the glycosaminoglycan fiber manufactured by using this novel method reveals the advantages of high extraction percentage, fine fibers, and showing white color. So that, the novel glycosaminoglycan fiber produced by using the present invention's method is suitable for being processed to an excipient.

(2) Moreover, comparing to the skin dressing produced by using a fabrication method proposed by Taiwan patent No. 442496 and the traditional skin dressing, the glycosaminoglycan fiber produced by using present invention's method is suitable for being processed to a (dry) skin dressing because of possessing an excellent absorption ability for tissue fluid.

(3) Furthermore, comparing to the skin dressing produced by using a fabrication method proposed by Taiwan patent No. 442496, the traditional skin dressing, and the commercial artificial skin, the glycosaminoglycan fiber produced by using present invention's method is suitable for being processed to a (wet) skin dressing, an artificial skin, or a hydrate mask because of possessing an excellent moisture retention capability.

The above description is made on embodiments of the present invention. However, the embodiments are not intended to limit scope of the present invention, and all equivalent implementations or alterations within the spirit of the present invention still fall within the scope of the present invention.

What is claimed is:

1. A method for manufacturing fungal pharmaceutical composition, comprising following steps:
   step (1): preparing a raw material of *Ganoderma lucidum* with a specific weight in a range from 200 g to 500 g, and then smashing the raw material of *Ganoderma lucidum* by pounding for 5-15 minutes, so as to obtain a smashed fungus;
   step (2): turning over the smashed fungus, and then tanning the smashed fungus for 5-30 minutes;
   step (3): spreading the smashed fungus, and then grinding the smashed fungus for obtaining a grinded fungus;
   step (4): immersing the grinded fungus in an organic solvent selected from the group consisting of methanol, ethanol and propanol;
   step (5): collecting a fungus residue from the organic solvent, and then drying the fungus residue under a first drying temperature in a range between 45° C. and 80° C.;
   step (6): applying a first alkali treatment to the fungus residue by using a first alkali solution for 20-40 minutes under specific processing conditions comprising a stirring speed of 120 rpm and a treating temperature of 80-100° C.; wherein the first alkali solution is mixed by 10-12N NaOH and 10-12N KOH according to a mixing ratio in a range from 1:11 to 1:5;
   step (7): applying a second alkali treatment to the fungus residue by using a second alkali solution for 2-8 hours under specific processing conditions comprising a stirring speed of 120 rpm and a treating temperature of 80-100° C.; wherein the second alkali solution is mixed by 1-5N NaOH and 1-5N KOH according to a mixing ratio in a range from 1:11 to 1:5;
   step (8): collecting the fungus residue by using a first filtering sieve, and then using water to wash the fungus residue;
   step (9): using deionized water to wash the fungus residue, and then collecting the fungus residue by using a second filtering sieve;
   step (10): applying a decoloring treatment to the fungus residue by using a bleaching agent for 80 minutes under specific processing conditions comprising a stirring speed of 120 rpm and a treating temperature of 80-100° C.; wherein the bleaching agent is hydrogen peroxide with concentration in a range between 25% and 45%; and
   step (11): using deionized water to wash the fungus residue, and then a fungal pharmaceutical composition is obtained.

2. The method for manufacturing fungal pharmaceutical composition of claim 1, wherein the fungal pharmaceutical composition obtained from the step (11) can be further processed to an artificial skin, a wound dressing, a mask, or an excipient.

3. The method for manufacturing fungal pharmaceutical composition of claim 1, wherein the raw material of *Ganoderma lucidum* prepared in the step (1) is selected from the group consisting of a fungal mycelium of *Ganoderma lucidum*, a fungal sporocarp of *Ganoderma lucidum*, or a post-extraction residue of the fungal mycelium.

4. The method for manufacturing fungal pharmaceutical composition of claim 1, wherein both the first filtering sieve and the second filtering sieve have a standard mesh number in a range between 20 and 80.

5. The method for manufacturing fungal pharmaceutical composition of claim 1, wherein the fungal pharmaceutical composition obtained from the step (11) is a glycosaminoglycan fiber, and the glycosaminoglycan fiber comprising N-acetylglucosamine and (1→3)-β-D-glucan.

6. The manufacturing fungal pharmaceutical composition of claim 5, further comprising
   step (12): applying a hot air drying treatment to the fungal pharmaceutical composition obtained from the step (11); and
   step (13): applying a vacuum freeze-drying treatment to the fungal pharmaceutical composition obtained from the step (121) after the temperature of the fungal pharmaceutical composition is cooled down.

* * * * *